US008611504B2

(12) United States Patent  
Kubiak et al.

(10) Patent No.: US 8,611,504 B2
(45) Date of Patent: Dec. 17, 2013

(54) ALIGNMENT PLATE APPARATUS AND METHOD OF USE

(75) Inventors: Erik Noble Kubiak, Salt Lake City, UT (US); Colin Edward Poole, Boise, ID (US)

(73) Assignee: Orthogrid Systems, LLC, Boise, ID (US)

( * ) Notice: Subject to any disclaimer, the term of this patent is extended or adjusted under 35 U.S.C. 154(b) by 0 days.

(21) Appl. No.: 13/805,069

(22) PCT Filed: Aug. 18, 2012

(86) PCT No.: PCT/US2012/051512
§ 371 (c)(1),
(2), (4) Date: Feb. 12, 2013

(65) Prior Publication Data
US 2013/0178863 A1  Jul. 11, 2013

Related U.S. Application Data

(60) Provisional application No. 61/525,259, filed on Aug. 19, 2011.

(51) Int. Cl.
| | |
|---|---|
| H05G 1/28 | (2006.01) |
| A61B 17/58 | (2006.01) |
| A61B 17/60 | (2006.01) |
| A61F 2/00 | (2006.01) |
| G01B 1/00 | (2006.01) |
| A61B 1/00 | (2006.01) |
| A61B 5/103 | (2006.01) |
| A61B 5/117 | (2006.01) |

(52) U.S. Cl.
USPC ........... 378/164; 378/162; 378/263; 606/102; 33/512

(58) Field of Classification Search
USPC .................. 606/102; 378/163, 164, 207, 162; 33/512; 250/576
See application file for complete search history.

(56) References Cited

U.S. PATENT DOCUMENTS

| | | | | | |
|---|---|---|---|---|---|
| 865,418 | A | * | 9/1907 | Moe | 33/2 R |
| 2,344,824 | A | * | 3/1944 | Landis | 378/164 |
| 3,547,121 | A | * | 12/1970 | Cherry | 604/116 |
| 3,770,956 | A | * | 11/1973 | Johnson | 378/164 |
| 4,918,715 | A | * | 4/1990 | Krupnick et al. | 378/164 |
| 4,953,193 | A | * | 8/1990 | Robinson | 378/162 |
| 4,985,019 | A | * | 1/1991 | Michelson | 604/180 |
| 5,020,088 | A | * | 5/1991 | Tobin | 378/164 |
| 5,030,223 | A | | 7/1991 | Anderson et al. | |
| 5,052,035 | A | * | 9/1991 | Krupnick | 378/163 |
| 5,105,457 | A | * | 4/1992 | Glassman | 378/163 |
| 5,260,985 | A | * | 11/1993 | Mosby | 378/164 |
| 5,285,785 | A | * | 2/1994 | Meyer | 600/426 |
| 5,690,108 | A | | 11/1997 | Chakeres | |
| 6,269,148 | B1 | | 7/2001 | Jessop et al. | |

(Continued)

OTHER PUBLICATIONS

PCT Notification of Transmittal of the International Search Report and the Written Opinion of the International Searching Authority, or the Declaration; Oct. 4, 2012.

*Primary Examiner* — David Bates
(74) *Attorney, Agent, or Firm* — Harris, Shelton, Hanover & Walsh; Susan B. Fentress

(57) ABSTRACT

A dimensioned grid apparatus for determining: 1) leg length, offset, and cup position during arthroplasty replacement surgery; 2) fracture reduction/correction position during trauma procedures and 3) an apparatus to be used for deformity correction planning is provided.

10 Claims, 9 Drawing Sheets

(56) References Cited

U.S. PATENT DOCUMENTS

| | | | |
|---|---|---|---|
| 6,366,643 B1 * | 4/2002 | Davis et al. | 378/154 |
| 6,690,767 B2 * | 2/2004 | Davis | 378/154 |
| 6,714,628 B2 | 3/2004 | Broyles et al. | |
| 6,723,097 B2 * | 4/2004 | Fraser et al. | 606/86 A |
| 6,839,402 B2 * | 1/2005 | Stabe et al. | 378/20 |
| 6,928,146 B2 * | 8/2005 | Broyles et al. | 378/164 |
| 7,127,826 B2 * | 10/2006 | Russell | 33/758 |
| 7,482,601 B2 | 1/2009 | Lewis et al. | |
| 7,508,919 B2 * | 3/2009 | Young et al. | 378/164 |
| 7,853,311 B1 * | 12/2010 | Webb | 600/426 |
| D664,661 S * | 7/2012 | Kubiak et al. | D24/171 |
| 8,215,957 B2 | 7/2012 | Shelton | |
| 8,235,594 B2 | 8/2012 | Carn | |
| 8,357,145 B2 | 1/2013 | Schleicher et al. | |
| 2004/0015176 A1 | 1/2004 | Cosman | |
| 2004/0068187 A1 | 4/2004 | Krause et al. | |
| 2004/0103903 A1 * | 6/2004 | Falahee | 128/849 |
| 2009/0129556 A1 * | 5/2009 | Ahn | 378/208 |
| 2010/0041979 A1 | 2/2010 | Harter | |
| 2010/0086185 A1 * | 4/2010 | Weiss | 382/131 |
| 2011/0103556 A1 | 5/2011 | Carn | |

* cited by examiner

ALIGNMENT PLATE APPARATUS AND METHOD OF USE

CROSS REFERENCE TO RELATED APPLICATIONS

This application claims the benefit of U.S. Provisional patent application 61/525,259, filed Aug. 19, 2011, and PCT/US12/51512 filed Aug. 18, 2012 under 35 U.S.C. §371 hereby specifically incorporated by reference in their entirety.

The present invention relates to a fluoroscopic alignment plate apparatus and method to use this apparatus in various orthopedic applications, such as, an anterior total hip arthroplasty.

BACKGROUND OF THE INVENTION

Many of the radiographic parameters essential to total hip arthroplasty (THA) component performance, such as wear, and stability, can be assessed intraoperatively with fluoroscopy. However even with intraoperative fluoroscopic guidance, the placement of an implant may still not be as close as desired by the surgeon. For example, malpositioning of the acetabular component during hip arthroplasty can lead to problems. For the acetabular implant to be inserted in the proper position relative to the pelvis during hip arthroplasty requires that the surgeon know the position of the patient's pelvis during surgery. Unfortunately, the position of the patient's pelvis varies widely during surgery and from patient to patient.

Various devices have been suggested to reduce malpositioning of these surgical components. For example, a transverse acetabular ligament has been suggested as a qualitative marker of the orientation of the acetabulum. (Archbold H A, et al. The Transverse Acetabular Ligament; an Aid to Orientation of the Acetabular Component During Primary Total Hip Replacement: a Preliminary Study of 1000 Cases Investigating Postoperative Stability, J Bone Joint Surg BR. 2006 July; 88(7):883-7. However, it has been suggested that the acetabulum may be deteriorated due to arthritis. Others have proposed using a tripod device that uses the anatomy of the ipsilateral hemi pelvis as the guide to position the prosthetic acetabular component. U.S. Patent Publication Number 20090306679. This instrument has three points. The first leg is positioned in the area of the posterior inferior acetabulum, a second leg is positioned in the area of the anterior superior iliac spine and a third leg is positioned on the ileum of the subject. U.S. Patent Publication Number 20090306679. However, a need exists in the industry for a device that is not implantable or invasive and is adaptable to a variety of applications.

SUMMARY OF THE INVENTION

The present invention, provides an apparatus and method for determining and measuring leg length, offset, and cup position during arthroplasty surgery by using a dimensioned grid plate positioned under the patient in conjunction with x-ray to measure variables, such as, hip implant position to determine the relative leg length and offset measurements for the implant. Arthroplasty surgery includes, for example: hip (anterior approach), hip (posterior approach), knee, ankle, elbow, and shoulder.

The apparatus of this invention includes a dimensioned radiolucent grid plate having a known quantifiable grid pattern which has geometry with known dimensioned symbols or numbers representing each or multiple grid lines. The dimensioned grid plate has a known angled grid line which may be any angle between about 30 and 60 degrees, preferably 45 degrees +/−15 degrees which are used for determination and alignment of the prosthetic acetabular cup position (version, abduction) in any and all x-ray views and a medial-lateral slot in the grid plate. At least one of a plurality of support plates are configured to retain the dimensioned grid plate and a central axis pin connected to at least one of the plurality of support plates. A medial lateral slot is configured to retain a pin and to allow medial-lateral translation of the grid plate relative to the support members and to rotate around the axis of the pin. This rotation is accomplished by the configuration of the medial lateral slot. The slot is made of a plurality countersunk grooves that are configured to retain the central axis pin. Additionally, the surface opposite one of the plurality of countersunk grooves is configured to retain a spring-loaded device. A plurality of spring-loaded devices mediate the movement of the grid.

In one embodiment, the present method employs x-rays to obtain an image that shows the position of the pelvis and both proximal femurs relative to the dimensioned grid plate. Subject specific data from an image of a patient consists of: data on a leg length, an off set and a cup position.

In another embodiment, a method to facilitate fracture reduction during a trauma procedure or to correct a deformity in a subject involves placing the dimensioned radiolucent grid plate apparatus adjacent to a patient during a procedure; and obtaining subject specific data from an image of the patient, wherein the data consists of a "Y" axis corresponding to an anatomical axis of the patient and an "X" axis corresponding to an angle related to an abnormality.

BRIEF DESCRIPTION OF THE SEVERAL VIEWS OF THE DRAWING

The drawing shows schematically a fluoroscopic alignment plate apparatus and method of use according to an example form of the present invention. The invention description refers to the accompanying drawings.

DESCRIPTION OF THE INVENTION

The present invention may be understood more readily by reference to the following detailed description of the invention. It is to be understood that this invention is not limited to the specific devices, methods, conditions or parameters described herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

These and other aspects, features and advantages of the invention will be understood with reference to the detailed description herein, and will be realized by means of the various elements and combinations particularly pointed out in the appended claims. It is to be understood that both the foregoing general description and the following detailed description of the invention are exemplary and explanatory of preferred embodiments of the inventions, and are not restrictive of the invention as claimed. Unless defined otherwise, all technical and scientific terms used herein have the same meaning as commonly understood by one of ordinary skill in the art to which this invention belongs.

Figure 1:
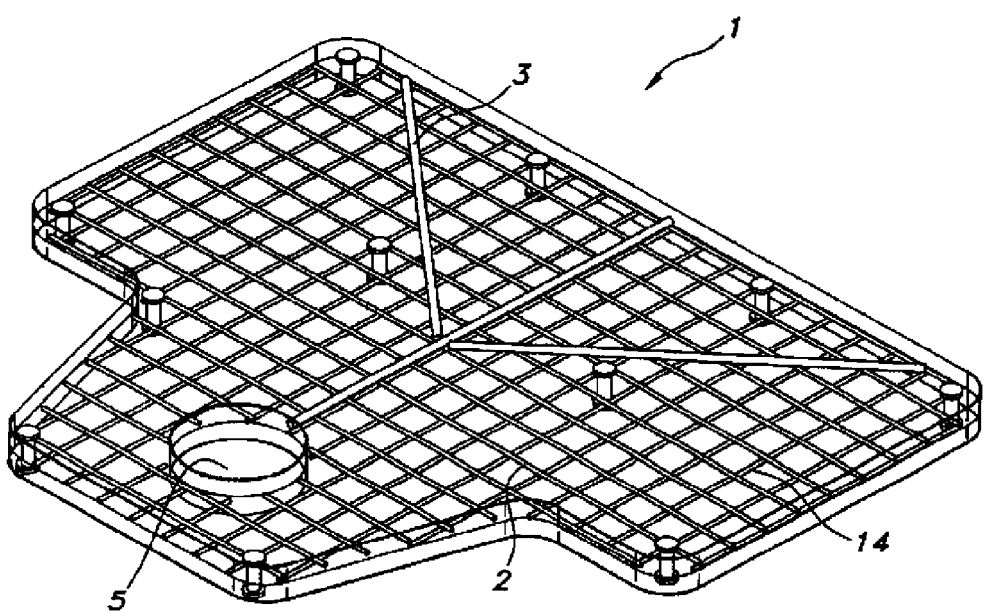
FIG. 1 is a perspective view of an embodiment of the dimensioned grid plate of the present invention.

Now referring to FIG. 1 a radiolucent dimensioned grid plate 1 is designed to be sufficiently large to ensure that the body part in questions, such as the entire pelvis and proximal femurs (left and right), is captured in a fluoro image. The radio-opaque grid (any and all metals, ceramics) has a (1 cm) quantifiable pattern (other quantifiable patterns, English) with each individual "block" having a square geometry. These grid lines align parallel to each other in two directions-vertical (cephalad/caudad) 14 and horizontal (medial/lateral) 2.

Figure 2:
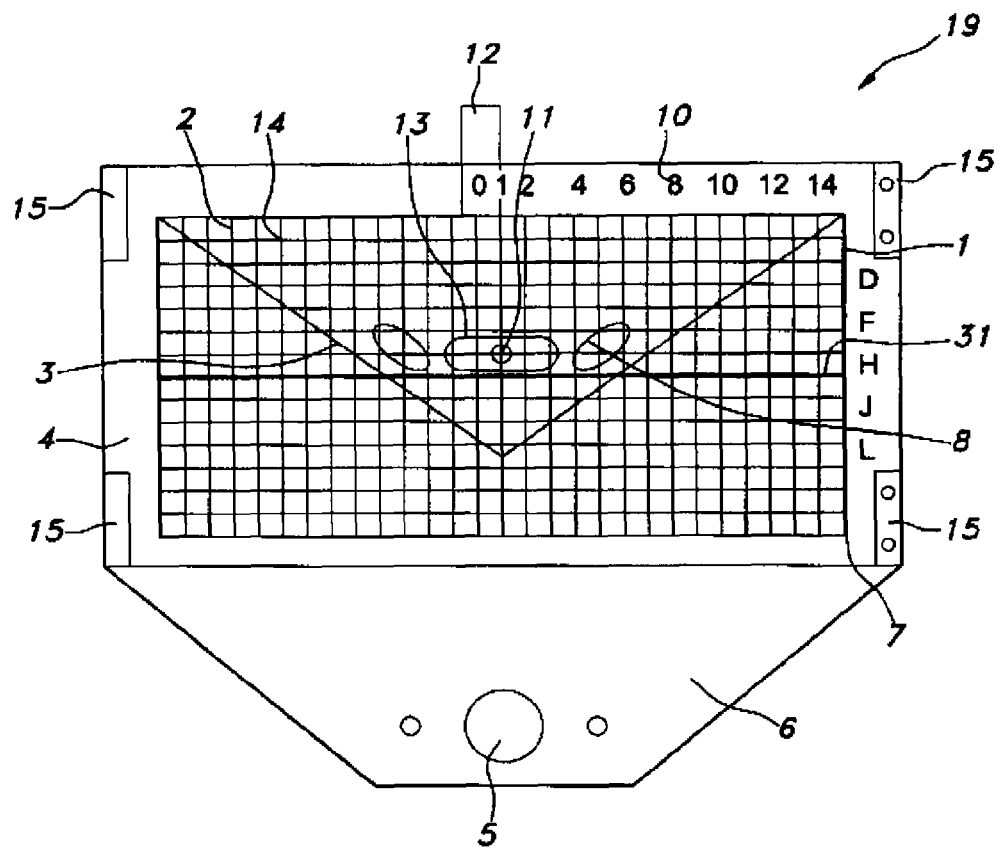
FIG. 2 is a front view of an embodiment of the dimensioned grid plate apparatus of the present invention.

Now referring to FIG. 2, a radiolucent dimensioned grid plate 1 for hip arthroplasty is provided. The dimensioned grid plate 1 is "sandwiched" between support plates 4 that have an extended aspect 6 in the caudal direction, to form the grid plate apparatus 19. This caudal aspect has a cutout 5 that matches and mates with an operating table's peg for use in an anterior approach procedure. The outer layer of the support plates 4 are joined together at the corners 15 by a solid metal piece that will also serve as the attachment place for the clamps that will attach the a dimensioned grid plate apparatus 19 to the operating table 72 or to the hip positioning apparatus (not shown). For strength, support rods (not shown) can be added to the caudal aspect.

In this dimensioned grid plate 1, two grid lines form a V and are angled at 45 degrees to the vertical and horizontal. In this dimensioned grid plate 1, these two lines represent a guide 3 for quantifying the abduction angle of an acetabular cup used during an arthroplasty procedure. However, the desired angle for the guide 3 relates to the type of implant. Metal on metal implants use a 40 degree angle of abduction, while polyethylene based articular surfaces use a 45 degree angle. The left half side of the grid plate apparatus 19 is a mirror image of the right hand side. The dimensioned grid plate 1 can have the following radio opaque markings (any and all methods of etching or marking): Two 45 degree angled radio opaque guide lines 3; two elliptical etchings which represent the proper version of the acetabular component 8 adjacent and cephalad to the 45 degree lines with a distance of approximately 20 cm from the apex of the two 45 lines (correlates to average standardized measurements of human pelvis between the radiolucent lines representing the quadrilateral surface, the roof of the obturator foramen, and the fossa acetabulae (the "teardrop")); numbers representing the vertical lines with zero being the midline and the numbers counted off in both medial and lateral directions from zero 10; letters of the alphabet on both sides of the grid representing the horizontal (x-axis) 9; and an image of an anatomical feature, such as a pelvis outline. All these grid lines and markings guide the physician in defining the orientation for insertion of the implants and specifically determining and measuring leg length, offset, cup placement, and femoral head center of rotation and mechanical axis of lower limb.

The dimensioned grid plate 1 is enclosed on either side in an epoxy resin that is both transparent and with a plurality of support plates 4 to form the grid plate apparatus 19. The epoxy creates a complete seal for the metal to prevent corrosion and support cleanability of the grid plate apparatus 19. Other manufacturing processes known to those skilled in the art include: laser etched: etched, then filled with radio-opaque marker in etched negative areas, then sandwiched; molded: with metal on support plates 4; using tungsten as the radio-opaque material for use in grid lines and numbers; sandwich deposition: printing process (like circuit boards); CNC Machined: back filled and radio-opaque decal: use of radio-opaque ink placed on support plates 4.

Figure 3:
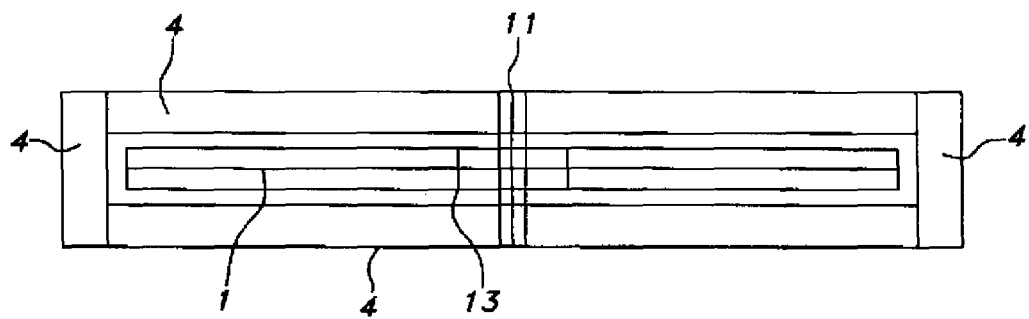
FIG. 3 is a side view of an embodiment of the dimensioned grid plate apparatus of the present invention.

Now referring to FIG. 3, the plurality of support plates 4 is shown surrounding the dimensioned grid plate 1. This central axis pin 11 is attached to the outer support plates 4, by conventional means such as a screw threaded through the support plate into the end of the axis pin 11. The axis pin 11 will be captured on either end by a screw threaded through the support plates 4 and into the end of the axis pin—on both ends. The medial-lateral slot 13 allows +/−5 cm medial-lateral translation of the dimensioned grid plate 1 relative to the support plates 4. The central axis pin 11 is oriented perpendicularly to the surface of the plurality of support plates 4 and the central axis pin 11 projects upwardly. This dimensioned grid plate 1 has a slot 13. The slot 13 allows the dimensioned grid plate 1 to be shifted from side to side or medially-laterally.

Figure 4A:
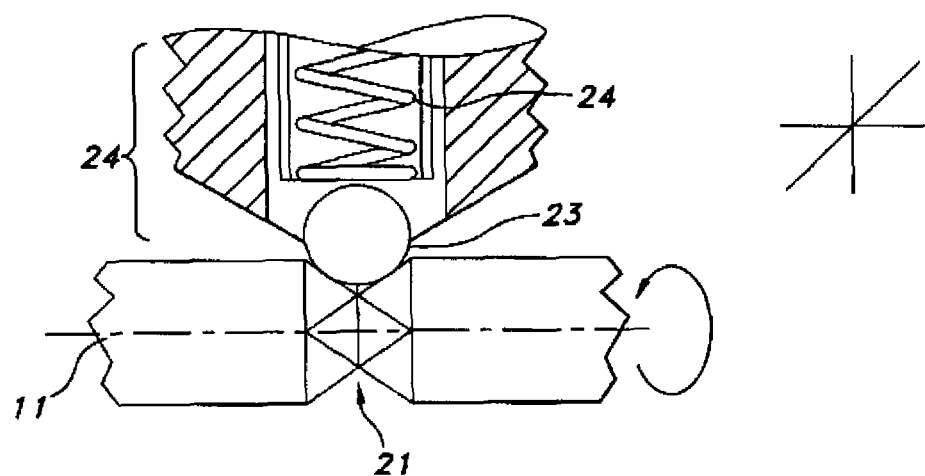
FIG. 4A is a side view of the apparatus of the apparatus of the present invention.
Figure 4B:
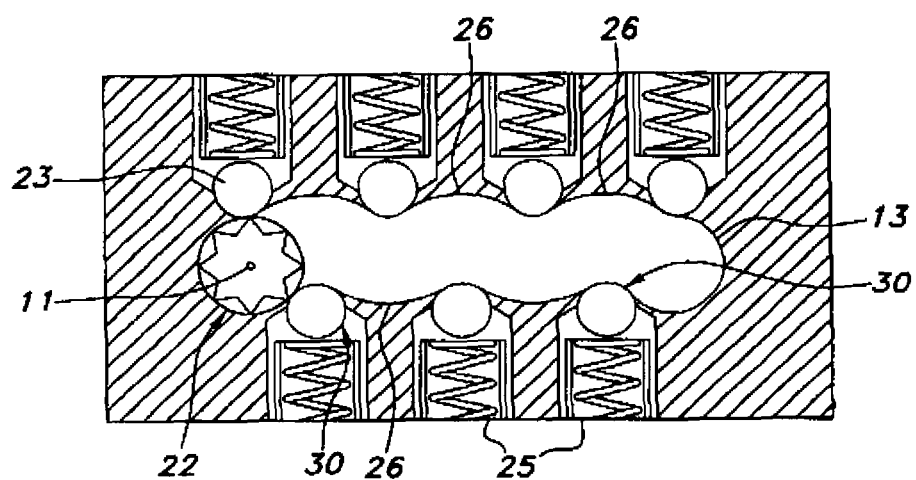
FIG. 4B is a top view of the translational/rotational mechanism of the present invention.

Now referring to FIGS. 4A and 4B, the dimensioned grid plate 1 articulates within the support plates 4 by a central axis pin 11. The medial-lateral slot 13 allows +/−5 cm medial-lateral translation of the dimensioned grid plate 1 relative to the support plates 4 and the patient 27. The dimensioned grid plate 1 can also be rotated +/−40 degrees about the central axis pin 11 axis relative to the support plates 4 and the patient 27. The dimensioned grid plate 1 is rotated or translated by using the handle 12 that is attached to the grid plate apparatus 19. The dimensioned grid plate 1 rotates about the central axis pin 11.

The slot 13 is configured with scalloped sides or edges that allow the dimensioned grid plate 1 to be indexed at a plurality of positions. The central axis pin 11 has a groove 21 about which the dimensioned grid plate 1 will rotate. The central axis pin groove 21 will further have a series of countersunk grooves 22 for engagement of spring-loaded ball 23 (for location of rotational position of the dimensioned grid plate 1 relative to the outer support plates. Furthermore, the dimensioned grid plate 1 translates in a medial lateral direction along the central axis pin 11. This translational movement is achieved by utilizing countersunk grooves 26 with a spring-loaded device (SLD) 24 having a uniform groove and countersunk slot configuration. The indexing is accomplished by a translation/rotational mechanism 25. The central axis pin 11 has the ability to translate along the medial-lateral slot 13 and engage in any one of a series of positions in the medial lateral direction. This is accomplished by having a plurality of spring-loaded device 25 used in conjunction with a plurality of corresponding countersunk slots 26. This rotation is accomplished by the configuration of the medial lateral slot 13.

The slot 13 is made of a plurality countersunk grooves 26 that are configured to retain the central axis pin 11. Additionally, the surface opposite 30 one of the plurality of countersunk grooves 26 is configured to retain a spring-loaded device 24. A plurality of spring-loaded devices 24 mediate the movement of the grid 1. The spring-loaded device 25 releasably holds the central axis pin 11 in the selected scalloped or notched position. The engagement/disengagement position and force will be determined based upon spring-loaded device holding capacity. The central axis pin 11 can be fluted longitudinally 22 which allows a rotational detent action as the patient (on the grid plate apparatus 20) is rotated in the horizontal plane about the central axis pin 1.

Figure 5:
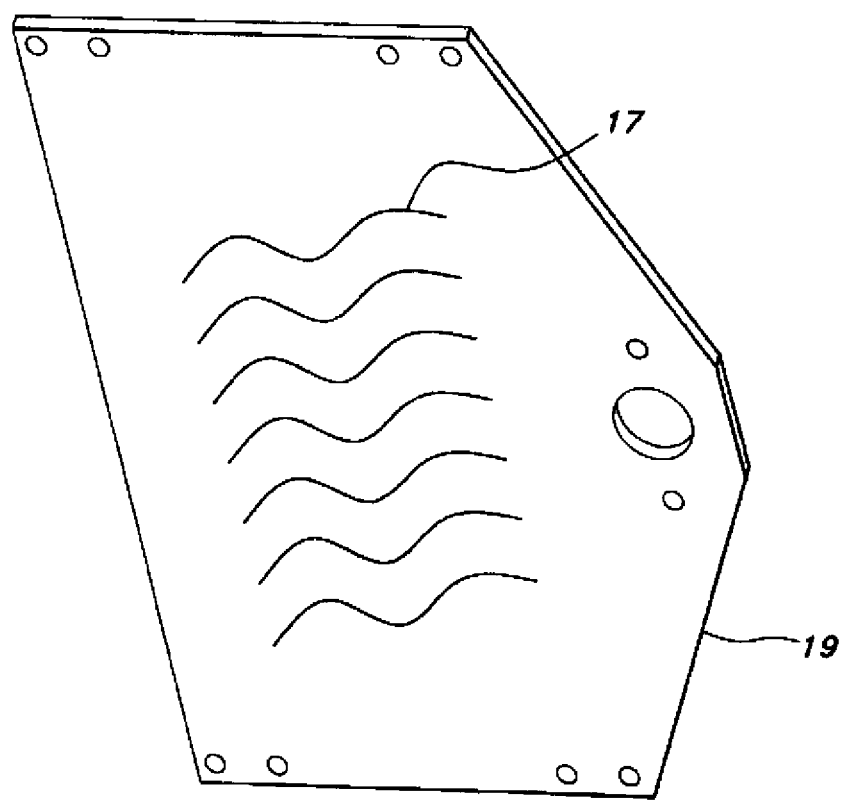
FIG. 5 is a rear view of an embodiment of the dimensioned grid plate apparatus of the present invention.

Now referring to FIG. 5, on the underside of the grid plate apparatus 19 there are strips of an adhesive material such as VELCRO 17 to further secure the plate to the table. This prevents the grid plate apparatus 19 from moving relative to the surgical table or patient during the surgical procedure.

Figure 6A:
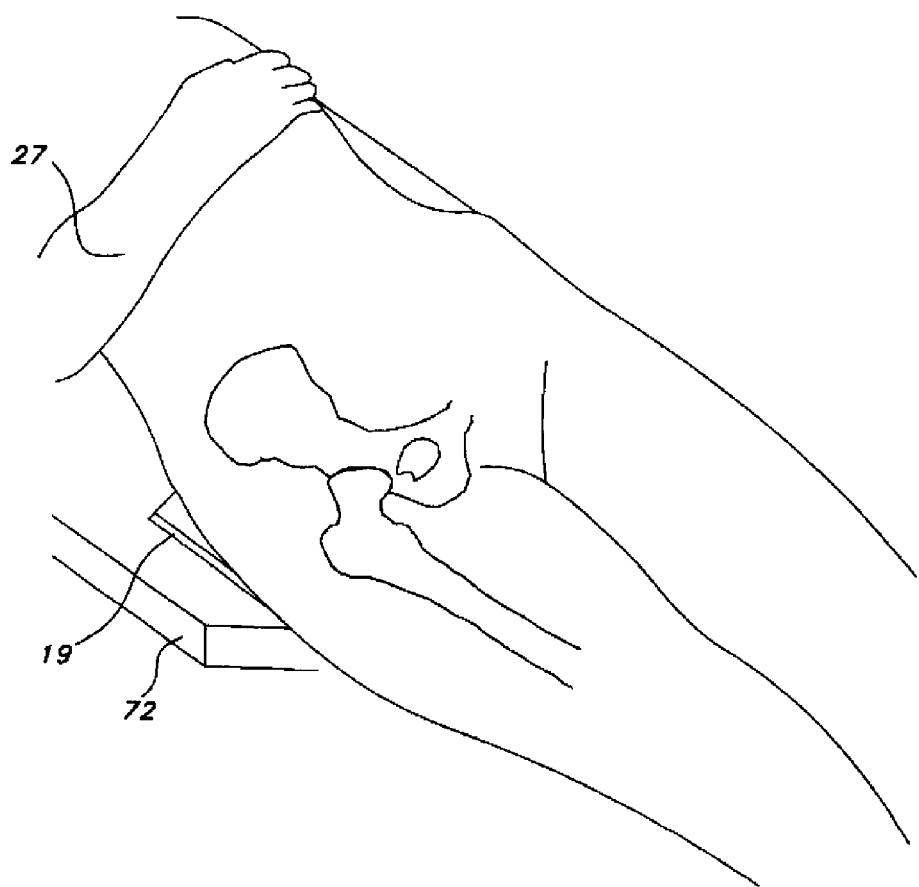
FIG. 6A is an illustrative sketch showing the relationship of the patient to the apparatus in an anterior approach.
Figure 6B:
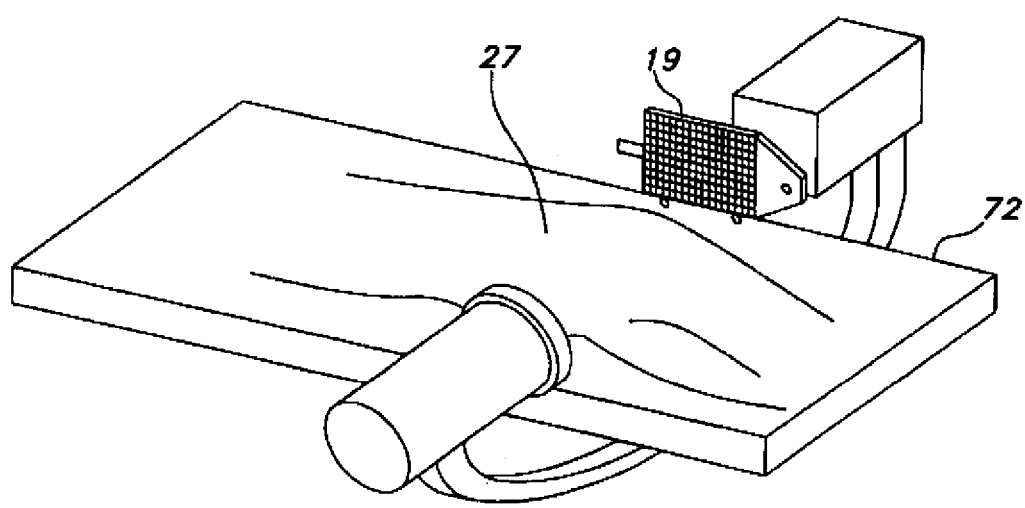
FIG. 6B is an illustrative sketch showing the relationship of the patient to the apparatus in an posterior approach.

Now referring to FIG. 6A, this embodiment allows for use in all surgical approaches to the hip. For the anterior approach, the grid plate apparatus 19 is used as shown in FIG. 6A, the patient is in a supine position with the grid apparatus 19 placed beneath the patient's pelvis. For the posterior approach as shown in FIG. 6B. the added benefit is having the ability to rotate, translate ML, and ideally position the grid to the anatomy of the patient. The dimensioned grid plate 1 has the ability to rotate +/−40 degrees from the vertical and translate in the medial lateral direction +/−5 cm. The dimensioned grid plate 1 can translate cephalad/caudad by adjusting the clamps which fix the dimensioned grid plate apparatus 19 to the bed or the hip positioning device. The rotational/translational grid can also be used for an anterior approach procedure. The Hilgenreiner's line 31 is a line drawn horizontally through the superior aspect of both triradiate cartilages. It should be horizontal, but is mainly used as a reference for Perkin's line and measurement of the acetabular angle.

The grid plate apparatus 19 has an extension in the caudad direction that has enough distance to allow the grid to lock onto the operating table 72 and then also ensure that the dimensioned grid plate apparatus 19 is directly behind (posterior) the patients' pelvis. The extension piece has a slot 5 cut out that matches the diameter of the peg (not shown) on the surgical table 72 that is being used. The peg (not shown) is fixed to the table and so by locking the peg to the plate there will be no motion of the plate 19 relative to the patient 27 during the surgery. In testing that was performed, tables that are conducive to the direct anterior approach were used. The present apparatus 1 and method can be used on any radiolucent operating table.

For a posterior surgical approach, FIG. 6B, the patient 27 is placed in the appropriate position for hip replacement surgery. The surgeon places the patient 27 in a Lateral Decubitus position; the surgeon positions the dimensioned grid plate 19 directly behind the pelvis of the patient 27. Once the surgeon has the trial implants or final implants inserted in the correct position inside the body, he or she will bring in the mobile x-ray machine (C-arm) and align the C-arm beam with the pelvis and grid plate in the anterior posterior plane. The image generated by the C-arm will provide a fluoro view of the anterior posterior pelvis and a grid pattern overlay. For the use in a posterior surgical approach, the patient 27 can be placed on his or her side in an appropriate and traditional manner. The surgeon will examine the x-ray image to determine subject specific data. Three parameters will be measured and determined at this point: 1) leg length, 2) offset, and 3) cup position.

Leg length: In quantifying leg length discrepancy, the patient's anatomical landmark(s) can be geometrically dimensioned relative to the grid lines. For example, points on the grid line drawn through the bottom of the ischium may be viewed as points on the grid marked along the H grid line. The proximal aspect of the left and right lesser trochanters may be viewed as points on the grid marked as G3 and F3 respectively.

The distance measured counting or using the grid squares between the ischial axis grid line and the respective two lesser trochanter points (G3 and F3 for example) is the leg length discrepancy.) Alternatively, a surgeon's preference may be to use points on the grid marking the greater trochanter in conjunction with the grid lines through the obturator foramina.

Offset. The offset of the femoral component is the distance from the center of rotation of the femoral head to a line bisecting the long axis of the stem.): In a similar technique to leg length, offset can be quantified. Corresponding radiographic points identified on the patient's left and right pelvis and proximal femur can be measured with the grid lines and blocks. The difference between the left and right measurements will quantify the offset mismatch and provide the surgeon with a numerical number to allow restoration of proper offset.

Pelvic Acetabular Implant commonly referred to as the "cup": The optimal position of the acetabular component can be determined using the dimensioned grid plate apparatus 19 as an alignment and measurement device. The dimensioned grid plate apparatus 19 has a 45 degree angled metal line 3. The radiographic image will display the trial or final implanted acetabular cup positioned in the acetabulum relative to the 45 degree guide line 3 that will be superimposed on the image. The cup position can then be adjusted based upon image feedback until correct positioning of the final implant is determined.

Figure 7:
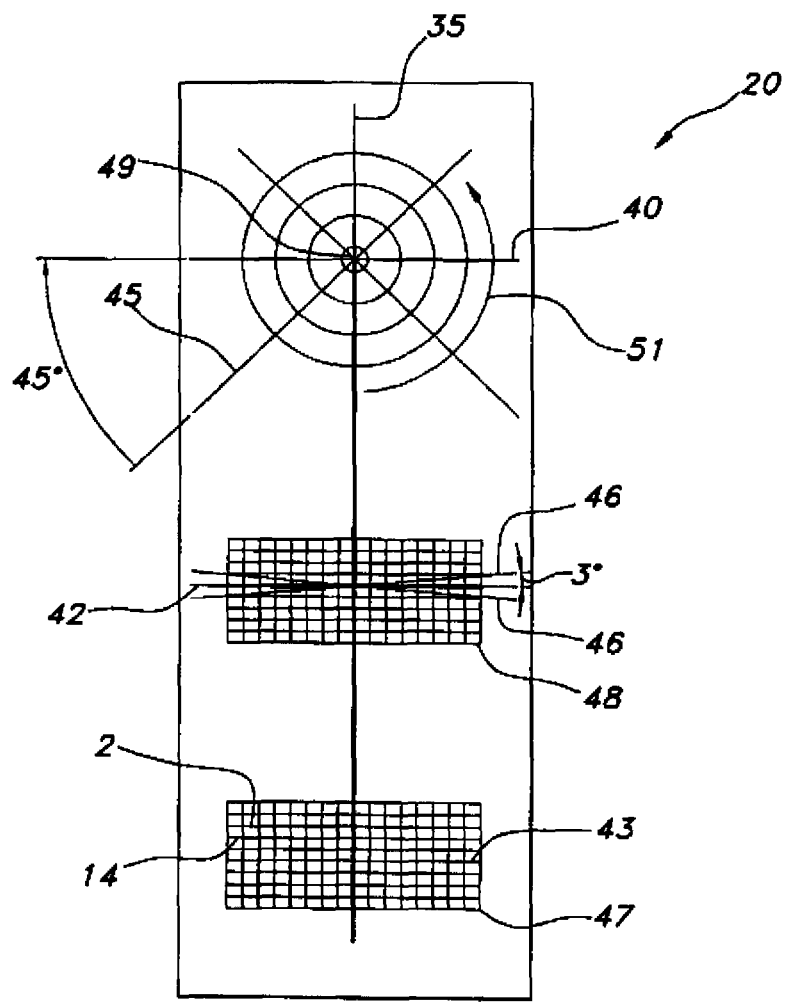
FIG. 7 is a front view of another embodiment of the dimensioned grid plate apparatus of the present invention.
Figure 8:
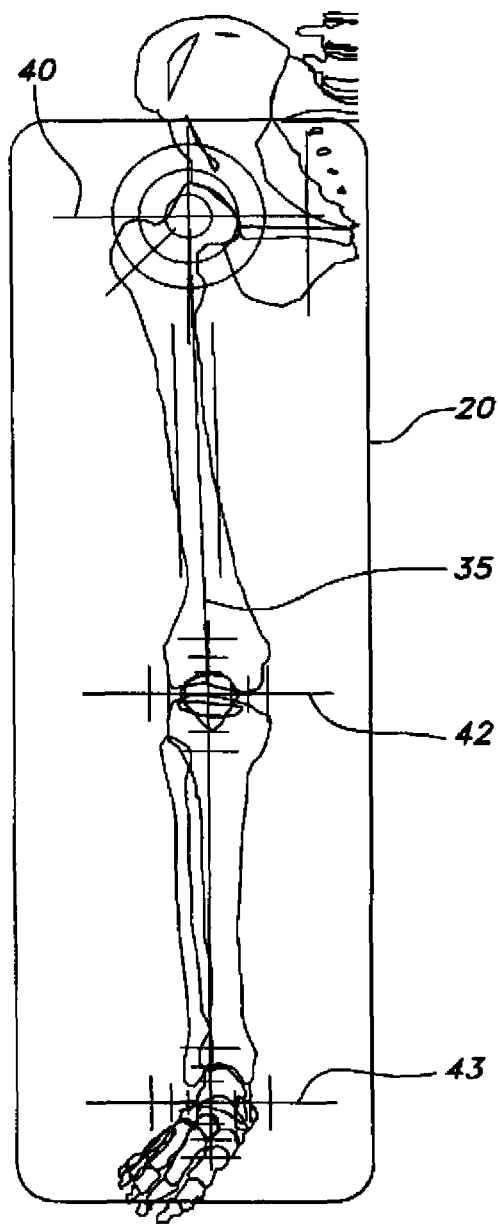
FIG. 8 is a sketch of x-ray view showing hip anatomy with implant and the grid overlay.

Now referring to FIGS. 7-8 a dimensioned grid plate 20 can be adapted for a variety of end-uses such as to facilitate the placement of an implant in arthroplasty or trauma procedure; for fracture reduction/correction during a trauma procedure or for deformity correction planning. In operation, the proximal femoral angle at 40 is determined. Next the distal femoral angle is determined at 42. Next the proximal tibial angle 42 is determined. Next the distal tibial angle 43 is determined to form the "X" axis relative to the "Y" axis 35 of the dimensional grid plate apparatus 20.

The Y axis 35 is the center line that creates a mirror image of grid and reference lines on either side of it, thus allowing use for either a left or a right leg application. 49 marks the center of the femoral head location. The proximal pelvic section of the device also has two 45 degree lines 45 that intersect at the center of the femoral head point 49. These same lines can also be used to quantify femoral neck angle 51. The knee section 48 is comprised of a grid pattern matching that of grid plate 20. Similarly, the ankle section is comprised of a grid pattern matching that of grid plate 20. The knee section has a central x-axis 42. Similarly, the ankle section has central x-axis 43. The knee grid section has two 3 degree lines 46 for use in quantifying alignment as needed.

In another embodiment, and now referring to FIG. 8, a dimensioned grid plate apparatus 20 for use with a trauma procedure on a lower extremity is disclosed. The trauma implications go beyond the pelvis and acetabulum. A larger grid plate 20 that runs from the patient's pelvis to beyond the ankle allows a surgeon to confirm length using the contralateral side. Additionally, the grid plate 20 allows the surgeon to confirm alignment prior to and after placement of an implant. The y-axis 35 correlates with the mechanical axis that runs from the head of the femur through bony landmarks in the tibial plateau through to the distal tibia. Angles that may create the x-axis 40 (depending upon fracture location) could be: proximal femoral angle; lateral distal femoral angle; medial proximal tibial angle; distal tibial angle.

Figure 9:
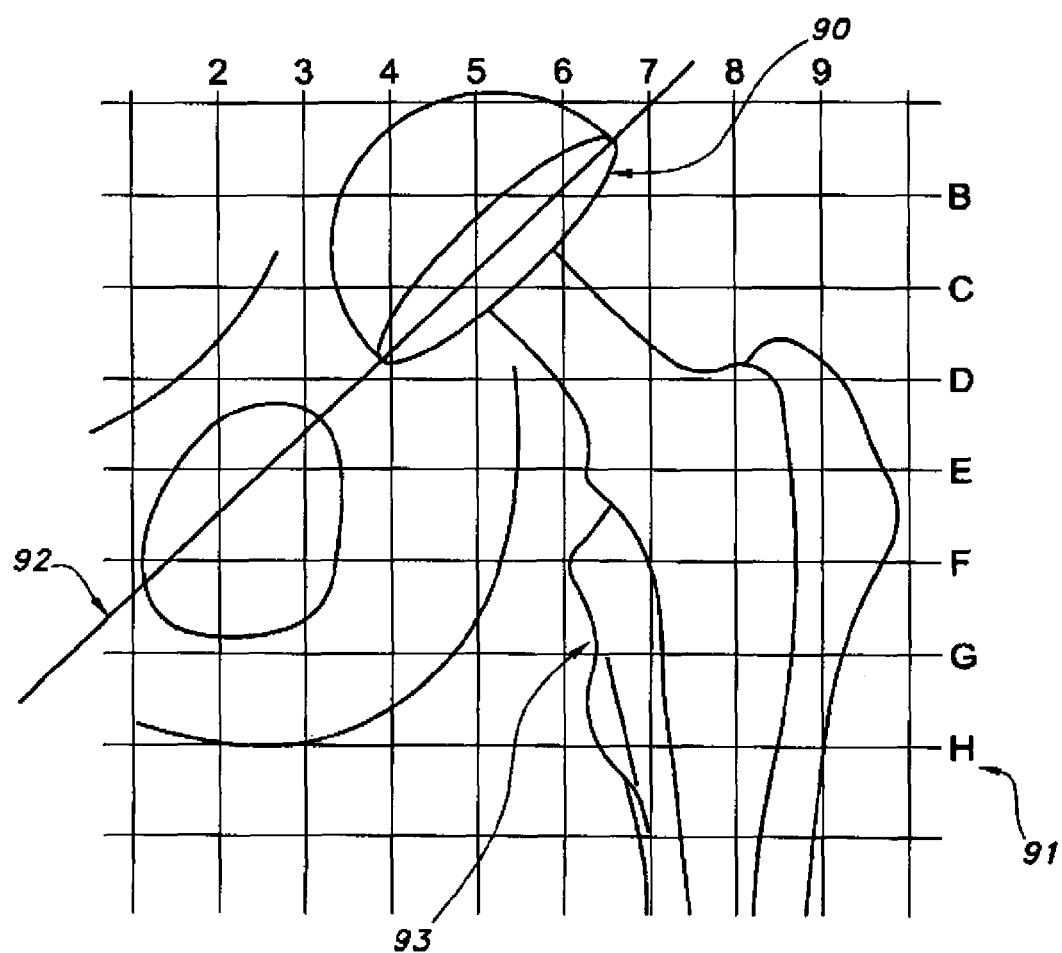
FIG. 9 is a schematic of an x-ray view of the hip anatomy with implant grid overview.

Now referring to FIG. 9, an x-ray view of hip anatomy within implant and grid overview is shown. In quantifying leg length discrepancy, the patient's anatomical landmark(s) can be geometrically dimensioned relative to the grid lines. For example, points on the grid line drawn through the bottom of the ischium may be viewed as points on the grid marked along the H grid line 91. For example the proximal aspect of the left lesser trochanters of the affected hip may be viewed as A point on the grid marked as G6.5 93 on the unaffected hip it can be determined that this same point is G5.5. For example, the distance measured counting or using the grid squares between the ischial axis grid line H 91 and the respective two lesser trochanter points (G6.5 and G5.5 for example) is the leg length discrepancy, relating to the inserted cup 90.

In another embodiment, deformity correction works much the same as the trauma description above. An existing deformity is evaluated against the patient's contralateral side. The grid plate apparatus 19 or 20 is used to ensure that the bone length and alignment correlate to the contralateral side. The grid plate apparatus 19 or 20 allows the surgeon to evaluate whether the osteotomy is sufficient to correct alignment and/or length intraoperatively, as well as making it visually easier to plan a correction procedure by using the grid to obtain pre-operative radiographs (i.e., surgeon does not have to draw his own lines and angles on plain radiographs to try to determine the appropriate amount of bone to remove and/or cut and re-angle).

CLINICAL STUDY Example: This retrospective cohort study reviews postoperative radiographic findings of 160 consecutive primary total hip athroplasties performed through an anterior supine approach with the aid of intraoperative fluoroscopy. The control group was 100 total hip athroplasties performed without the grid plate apparatus 19 or 20. The study group was 54 total hip athroplasties performed with the use of the grid plate apparatus 19 or 20 to aid in assessing acetabular component inclination, femoral offset, and leg length. Femoral offset, component abduction and leg length differences were measured by two readers blinded to the group status. Surgeon aims included an inclination angle of 40-45 degrees and a leg length and offset equal to the contralateral side. Additionally, the two groups were assessed for differences in demographics and clinical outcomes including complications such as dislocation and symptomatic leg length discrepancy.

Results

Inclination angle averaged 42 degrees (SD 1.5 degrees) for the grid group compared to 45 degrees (SD 4 degrees).

Femoral offset averaged +1.5 mm (SD 1 mm) compared to the contralateral side for the grid group compared to −1 mm (SD 3 mm) for the control group.

Leg length differences averaged +1.5 mm (SD 1 mm) compared to the contralateral side for the grid group compared to −1 mm (SD 3 mm) for the control group.

There were no statistically significant differences in age, gender, BMI or dislocation rate between groups. However, the group using the grid plate apparatus 20 had a lower rate of symptomatic leg length discrepancy than the control group.

CONCLUSIONS

While intraoperative use of fluoroscopy to guide femoral offset, leg length and acetabular inclination is helpful, a radiopaque guide with abduction angle references can be helpful to improve precision and accuracy in accomplishing the orthopedic surgeon's goals.

While the invention has been described with reference to preferred and example embodiments, it will be understood by those skilled in the art that a variety of modifications, additions and deletions are within the scope of the invention, as defined by the following claims.

The invention claimed is:

1. An apparatus comprising:
a radiolucent dimensioned grid plate having a top surface and a bottom surface, at least one of the top and bottom surfaces having a plurality of dimensioned radio-opaque horizontal and vertical lines formed thereon, the horizontal and vertical lines being spaced apart as in a grid pattern with identical distance between each subsequent vertical line in a horizontal direction and each subsequent horizontal line in a vertical direction, and an oblique grid line at an angle of between about 30 to 50 degrees relative to the horizontal lines, and a medial-lateral slot formed in one of the top and bottom surfaces of said grid plate to be parallel to the horizontal lines;
at least one of a plurality of support plates configured to retain said dimensioned grid plate by receiving one of the top and bottom surface on a front or back surface of at least one of the plurality of support plates; and
a central axis pin connected to at least one of said plurality of support plates perpendicularly relative to a plane of the at least one support plates,
wherein said medial-lateral slot is configured to retain the central axis pin therethrough,
wherein the medial-lateral slot is configured to allow medial-lateral translation of the grid plate relative to a horizontal line of said support plates, the horizontal line being generally aligned with the medial-lateral slot,
wherein the medial-lateral slot is configured to allow the grid plate to rotate around the axis of said central axis pin relative to the support plates, and
wherein the medial-lateral slot is comprised of a plurality countersunk grooves that are configured to retain said central axis pin to the grid plate.

2. The apparatus of claim 1 wherein the surface opposite the one of the plurality of countersunk grooves in the to surface or bottom surface of the grid plate is configured to retain a spring-loaded device.

3. The apparatus of claim 1 wherein said plurality of support plates have an extended portion including a hole extending through the plurality of support plates coaxially, the hole being sized to accommodate an operating table peg for attaching the support plates to an operating table.

4. The apparatus of claim 1 further comprising said grid plate having a plurality of radio-opaque elliptical figures representing an acetabular component.

5. The apparatus of claim 1 further comprising a radio-opaque image of an anatomical feature on said grid, the anatomical feature being a pelvis outline.

6. The apparatus of claim 1 further comprising an adhesive material applied to the bottom surface of at least one of the plurality of support plates to secure said apparatus to an operating table.

7. A method to facilitate intraoperative placement of a prosthetic device in a subject during an arthroplasty procedure of bones of a leg of the subject, the method comprising:
   implanting the prosthetic device into the patient;
   placing the apparatus of claim 1 adjacent to the leg of the subject;
   generating a radiographic image of the bones such that both the radio-opaque lines and the bones are present in the radiographic image;
   obtaining subject specific data from the radiographic image of said subject, wherein said data consists of:
      a leg length, found by measured counting or using the grid squares between an axis grid line at the ischium and the respective two lesser trochanter points in the radiographic image;
      an offset, found by measured counting or using the grid squares from the center of rotation of the femoral head to a line bisecting the long axis of the stem; and
      a cup position, found by using the apparatus to compare position of the oblique grid line in the radiographic image to the acetabulum; and
   adjusting the placement of the prosthetic device based on the subject specific data.

8. A method to facilitate correction of an orthopedic abnormality of a bone in a subject comprising:
   placing the apparatus of claim 1 adjacent to the subject;
   generating a radiographic image of the bone such that the radio-opaque lines and the bone are present in the radiographic image;
   obtaining subject specific data from the radiographic image of said subject, wherein said data consists of a "Y" axis indicating an anatomical axis of said subject and an "X" axis indicating the angle of the longitudinal axis of the bone with the abnormality; and
   performing an arthroplasty procedure on the bone to correct the orthopedic abnormality by causing the "X" axis of the bone to align with the "Y" axis of the bone.

9. The method of claim 8 where in the abnormality of the bone is a deformity of the bone.

10. The method of claim 8 where in the abnormality of the bone is a fracture of the bone due to trauma.

\* \* \* \* \*

UNITED STATES PATENT AND TRADEMARK OFFICE
CERTIFICATE OF CORRECTION

Page 1 of 1

PATENT NO. : 8,611,504 B2
APPLICATION NO. : 13/805069
DATED : December 17, 2013
INVENTOR(S) : Kubiak et al.

It is certified that error appears in the above-identified patent and that said Letters Patent is hereby corrected as shown below:

In the Claims

Column 8, lines 53-56 should read

2. The apparatus of claim 1 wherein the surface opposite the one of the plurality of countersunk grooves in the top surface or bottom surface of the grid plate is configured to retain a spring-loaded device.

Signed and Sealed this
Twenty-seventh Day of May, 2014

Michelle K. Lee
*Deputy Director of the United States Patent and Trademark Office*